(12) United States Patent
Bell et al.

(10) Patent No.: US 9,482,657 B2
(45) Date of Patent: Nov. 1, 2016

(54) FORMULATION OF COMPLEX COATING MIXTURES WITH EFFECT PIGMENTS

(71) Applicant: PPG Industries Ohio, Inc., Cleveland, OH (US)

(72) Inventors: Steve Bell, Oxford (GB); Phil Haskings, Llandysul (GB)

(73) Assignee: PPG Industries Ohio, Inc., Cleveland, OH (US)

( * ) Notice: Subject to any disclaimer, the term of this patent is extended or adjusted under 35 U.S.C. 154(b) by 327 days.

(21) Appl. No.: 14/073,976

(22) Filed: Nov. 7, 2013

(65) Prior Publication Data

US 2015/0127269 A1    May 7, 2015

(51) Int. Cl.

| | |
|---|---|
| *G01N 33/32* | (2006.01) |
| *G01N 21/55* | (2014.01) |
| *G01J 3/50* | (2006.01) |
| *G01J 3/46* | (2006.01) |
| *G01N 21/47* | (2006.01) |
| *G01N 21/25* | (2006.01) |
| *G01N 21/84* | (2006.01) |
| *G01N 21/57* | (2006.01) |

(52) U.S. Cl.
CPC .............. *G01N 33/32* (2013.01); *G01J 3/463* (2013.01); *G01J 3/504* (2013.01); *G01N 21/255* (2013.01); *G01N 21/4738* (2013.01); *G01N 21/8422* (2013.01); *G01N 2021/575* (2013.01); *G01N 2021/8427* (2013.01)

(58) Field of Classification Search
CPC ............. G01N 33/32; G01N 21/8422; G01N 2021/8427; G01N 21/255; G01N 21/4738; G01N 2021/575; G01J 3/463; G01J 3/504
USPC ................. 702/22; 428/623; 427/8; 118/712; 141/83
See application file for complete search history.

(56) References Cited

U.S. PATENT DOCUMENTS

| | | | | |
|---|---|---|---|---|
| 4,775,420 A | * | 10/1988 | Gonnet ................. | D21H 19/58 106/447 |
| 5,231,472 A | * | 7/1993 | Marcus .............. | G01N 21/4738 356/402 |
| 5,663,025 A | * | 9/1997 | Ciccarelli ............ | G03G 9/0914 430/108.21 |
| 5,740,079 A | | 4/1998 | Shigemori et al. | |
| 5,824,373 A | * | 10/1998 | Biller ...................... | B05D 7/08 427/474 |
| 5,877,231 A | * | 3/1999 | Biller ...................... | B05D 7/08 522/14 |
| 5,929,998 A | * | 7/1999 | Kettler ...................... | G01J 3/46 356/405 |
| 7,045,169 B2 | * | 5/2006 | Freeman .............. | G05B 13/048 106/632 |
| 7,056,969 B2 | * | 6/2006 | Cuch ........................ | B41M 5/52 524/425 |
| 7,466,415 B2 | * | 12/2008 | Gibson ............... | B01F 13/1055 356/402 |
| 7,991,596 B2 | | 8/2011 | Steenhoek | |

(Continued)

FOREIGN PATENT DOCUMENTS

| | | |
|---|---|---|
| CN | 101542271 A | 9/2009 |
| TW | 321720 B | 12/1997 |

*Primary Examiner* — Carol S Tsai
(74) *Attorney, Agent, or Firm* — Brad Barger; Mike Frodsham

(57) ABSTRACT

A computer implemented method. The method includes obtaining, using a processor, reflectance data from a target coating and calculating, using the processor, a reflectance from the data, wherein calculating comprises performing a calculation using a radiative transfer equation. The method also includes generating, using the processor and based on the reflectance, a coating formulation that is the same or substantially similar in appearance to the target coating.

15 Claims, 7 Drawing Sheets

(56) References Cited

U.S. PATENT DOCUMENTS

| | | | | |
|---|---|---|---|---|
| 8,271,242 B2* | 9/2012 | Berlin | G01J 3/46 | 703/6 |
| 8,913,238 B2* | 12/2014 | Kettler | G01J 3/50 | 356/243.1 |
| 8,922,775 B2* | 12/2014 | Kettler | G01J 3/524 | 356/421 |
| 8,934,099 B2* | 1/2015 | Kettler | G01J 3/50 | 356/421 |
| 2003/0124244 A1* | 7/2003 | Freeman | G05B 13/048 | 427/8 |
| 2003/0162009 A1* | 8/2003 | Cuch | B41M 5/52 | 428/306.6 |
| 2006/0181707 A1* | 8/2006 | Gibson | B01F 13/1055 | 356/402 |
| 2009/0319111 A1* | 12/2009 | Tu | B60L 1/00 | 701/22 |
| 2013/0201476 A1* | 8/2013 | Beymore | G01J 3/463 | 356/319 |
| 2013/0201847 A1 | 8/2013 | Chincholi et al. | | |
| 2013/0242306 A1* | 9/2013 | Kettler | G01J 3/524 | 356/421 |
| 2013/0250291 A1* | 9/2013 | Kettler | G01J 3/50 | 356/306 |
| 2013/0258331 A1* | 10/2013 | Kettler | G01J 3/50 | 356/243.1 |
| 2014/0017392 A1* | 1/2014 | Lewis | B01F 13/1066 | 427/8 |
| 2014/0278253 A1* | 9/2014 | Beymore | G06N 7/005 | 702/189 |
| 2014/0278254 A1* | 9/2014 | Beymore | G06N 7/005 | 702/189 |
| 2015/0156384 A1* | 6/2015 | Rhoads | G06K 9/2063 | 348/207.11 |

\* cited by examiner

FORMULATION OF COMPLEX COATING MIXTURES WITH EFFECT PIGMENTS

FIELD OF THE INVENTION

In various embodiments, the present invention generally relates to a method and apparatus for identifying physical property attributes, such as effect pigments, of cured complex coating (e.g., paint) mixtures.

BACKGROUND OF THE INVENTION

Radiative transfer deals with electromagnetic wave propagation and is often difficult to model because it requires elaborate calculations. The traditional technique for the formulation of complex coating (e.g., paint) mixtures for the purpose of color matching is Kubelka-Munk Theory. The Kubelka-Munk method is used to calculate a two-flux approximation for solving the complicated equations in radiative transfer theory. Such an approximation is oftentimes inadequate for formulating complex coating mixtures that contain metallic, pearlescent, and other special effect pigments.

The underlying idea for the two-flux approximation is to find the diffuse radiance while solving the full radiative transfer equation. The approximation comes in with the approach to the full equation, however, because radiation fluxes are treated as angular-averaged properties, so one assumes that the details of the variation of the intensity are not very important for the predictions of these quantities, i.e. the parameters of color do not travel with viewing angle.

Many formulation strategies operate by working through every combination of, for example, four tinters out of ten, and determining the best match possible with each combination, and then looking for the best of the group. Other formulation strategies rely on neural networks, which reduce computation time, but are still fundamentally brute-force strategies.

Thus, a need exists for systems and methods that are suitable for analyzing complex coating mixtures containing effect pigments, for example metallic and pearlescent pigments.

SUMMARY OF THE INVENTION

In a first aspect, embodiments of the invention provide a computer implemented method. The method includes obtaining, using a processor, reflectance data from a target coating and calculating, using the processor, a reflectance from the data, wherein calculating comprises performing a calculation using a radiative transfer equation. The method also includes generating, using the processor and based on the reflectance, a coating formulation that is the same or substantially similar in appearance to the target coating.

In another aspect, embodiments of the invention are directed to a system. The system includes a database. The system also includes a processor in communication with the database and programmed to obtain reflectance data from a target coating; calculate a reflectance from the data, wherein calculating comprises performing a calculation using a radiative transfer equation; and generate, based on the reflectance, a coating formulation that is the same or substantially similar in appearance to the target coating.

In another aspect, embodiments of the invention provide an apparatus. The apparatus includes means for obtaining reflectance data from a target coating and means for calculating a reflectance from the data, wherein calculating comprises performing a calculation using a radiative transfer equation. The apparatus also includes means for generating, based on the reflectance, a coating formulation that is the same or substantially similar in appearance to the target coating.

In a further aspect, embodiments of the invention provide a non-transitory computer readable medium including software for causing a processor to: obtain reflectance data from a target coating; calculate a reflectance from the data, wherein calculating comprises performing a calculation using a radiative transfer equation; and generate, based on the reflectance, a coating formulation that is the same or substantially similar in appearance to the target coating.

DETAILED DESCRIPTION OF THE INVENTION

Figure 1:
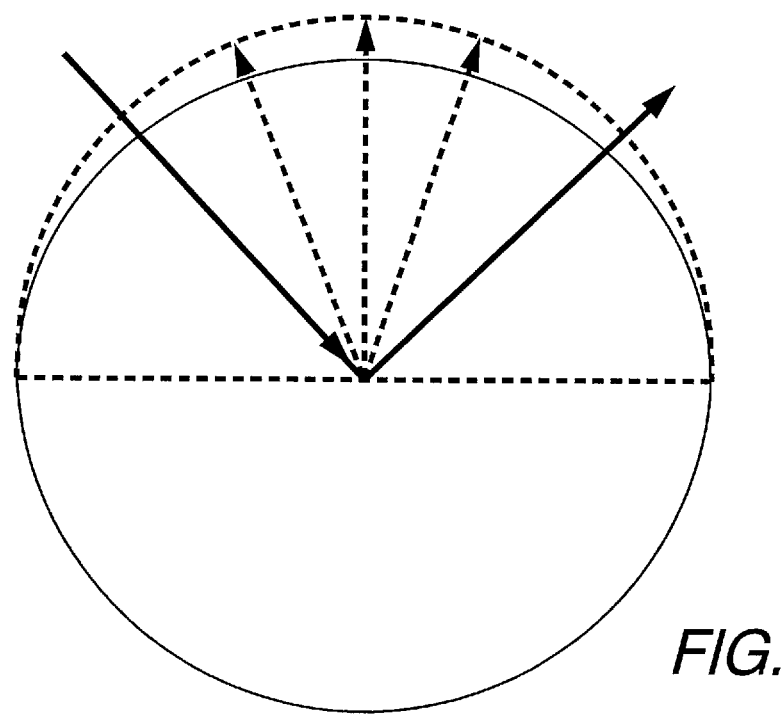
FIG. 1 illustrates industry standard angles between the incident electromagnetic wave path and specular reflection electromagnetic wave path.

In various aspects, embodiments of the invention include a spectrophotometer and methods that may be used to identify effects that are present in a coating composition on a target sample. Various embodiments of the invention include an apparatus that has a device for capturing information for a target sample and a processor for identifying bulk effects that can be used to produce a coating mixture that has a texture that is the same as or substantially similar, at least in appearance, to the target sample. An output device may be used for conveying the bulk effect information to a user.

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Embodiments of the invention are directed generally to spectral analysis of coatings, and more particularly, but not by way of limitation, to devices, methods and systems for predicting and formulating a complex coating mixture containing metallic, pearlescent, and/or special effect pigments.

Various embodiments of the present invention are directed to systems and methods for electromagnetic wave propagation that include modeling wave propagation in an electromagnetic wave path through a multilayer pigment; modeling the coating at the multilayer pigment; and optionally replacing the calculation at the multilayer pigment with a further multilayer pigment calculation. In an example, replacing the calculation at the multilayer pigment with a further multilayer pigment calculation includes a model of continuing electromagnetic propagation in the wave path to model more complex interactions between the electromagnetic wave and the multilayer pigment while replacing the multilayer pigment.

Radiative transfer problems typically involve scattering, which implies that the source function itself relies on the electromagnetic radiation field. The mathematics of this is an integro-differential equation of transfer, which for realistic media with complex multiple scattering effects uses numerical methods. For these cases of scattering, the formal solution does not provide an explicit solution, although it may be used to reformulate the problem as an integral equation as follows:

$$\mu \frac{\partial I(\tau, \mu, \varphi)}{\partial \tau} = I(\tau, \mu, \varphi) - \frac{1}{4\pi} \int_{-1}^{+1} \int_{0}^{2\pi} p(\mu, \varphi; \mu' \varphi') I(\tau, \mu', \varphi') d\mu' d\varphi' \quad (1)$$

The phase function $p(\mu, \phi; \mu' \phi')$ describes the scattering from direction $(\mu, \phi)$ into $(\mu' \phi')$. $\mu$ and $\phi$ are descriptors of the zenithal and azimuthal angles respectively. Equation (1) shows the influence of scattering in that the intensity in one direction depends on the intensity in all other directions. Approximations are often used to bypass the radiative transfer calculation because of such scattering effects.

An approximation theory for scattering in the bulk is to treat the strong single scattering from the specular angle as exact while taking into account the interaction with an angularly averaged diffuse intensity produced primarily from the ordinary pigment scattering.

In various embodiments, the form of the radiative transfer equations is made more suitable to coatings and, in various embodiments, to a numerical solver. In various embodiments, a form of the radiative transfer equation may be used to manually split the total intensity, which includes the incident collimated light from the goniospectrophotometric device lamp, and the diffuse multiple scattering term.

In various embodiments, the use of an isotropic factor, g, may be used to specify the phase function such that calculation of the expectation value for $\mu$ returns exactly the same value g. In various embodiments, the geometries considered are either semi-infinite, extending in optical depth from $\tau=0$ to $\tau=\infty$, or finite, extending from $\tau=0$ to $\tau=\tau_1$, which depends on the coating and substrate.

The situation may be more complex for aluminum pigments, because scattering from such pigments is a mirror like-reflection from their surfaces. Geometrical optics may be used to describe their properties, and because the orientation of the aluminum is not complete, an orientation distribution function may be introduced, which in various embodiments is the fraction of flakes in the solid angle $d\Omega$ in the direction $\theta$.

In various embodiments, the attenuation may be found from the projected cross-sectional area presented to an incoming beam. The phase function may be determined by the orientation distribution function. The probability of scatter is dependent on a projected area which is related to the angle between incident and the flake normal. Separate phase functions may be used for aluminum and pearlescent flakes in various embodiments. For pearlescent flakes, the phase function may be derived accurately using Fresnel equations which are presented, for example, in "Classical Electrodynamics," J. D. Jackson, ISBN-10: 047130932X, which is incorporated herein by reference.

In various embodiments, the solutions to radiative transfer equations may be fed back into the calculation on the reflectance of an unknown complex coating mixture (i.e., formulation or recipe). The identification of which tinters to use from a selection of tinters and how much of each to use is determined. Embodiments of the invention optimize the match for a given palette of tinters, rather than working through every combination of a limited set of toners to find the best match possible.

In various embodiments the difference between the predicted reflectance and the measured reflectance is minimized. The difference may be modified by the use of a weighting factor. Such a calculation may be more efficient than a combinatorial approach, which requires factorial iterations through an entire toner list. In various embodiments, the calculation may reduce metamerism as compared to a colorimetric solution such as, for example, LabCH.

In various embodiments, a pruning method may be used to achieve a minimum number of toners in a coating recipe. In various embodiments the pruning method sets the limit for the minimum toner concentration or finds and removes tinters from, for example, a Taylor series vector expansion.

In various aspects, embodiments of the invention include a goniospectrophotometric device that measures spectral data at angles that include, but are not limited to, industry standard angles between the incident electromagnetic wave path and specular reflection electromagnetic wave path, as illustrated in FIG. 1.

Various embodiments of the invention include any apparatus that has a device for capturing spectral electromagnetic wave information from reflection off a sample, such as a goniospectophotometric device, and a processor that performs radiative transfer calculations (e.g., a personal computer or any type of computing device).

In various embodiments, the systems and methods of the present invention find an optimal goniospectrophotometric match over a palette, which can be the entire mixing scheme if desired. A representative portion of the electromagnetic spectrum may be taken from a goniospectrophotometric device. The goniospectrophotometric device may collect reflectance data as an array of detectors spread throughout the angular geometry space, for example as illustrated in FIG. 2, or as an array of light sources spread throughout the angular geometry space focused into a set of detectors.

Embodiments of the present invention provide for color matching of metallic, pearlescent, and special effect pigments using the theory of light scattering, which relates pigment optical properties to the spectral and angular reflectance characteristics as a function of concentration. In an example that may be implemented for metallic pigment color matching, an approximate theory for the scattering in the bulk, which treats the strong single scattering from the pigment exactly but which also takes into account the interaction with angularly average diffuse intensity produced predominately from non-effect toner scattering, may be used. In another example, a multi-flux theory of light scattering may be turned to the attenuation, thus circumventing the need to make significant approximations at any stage of the coating formulation.

Figure 3:
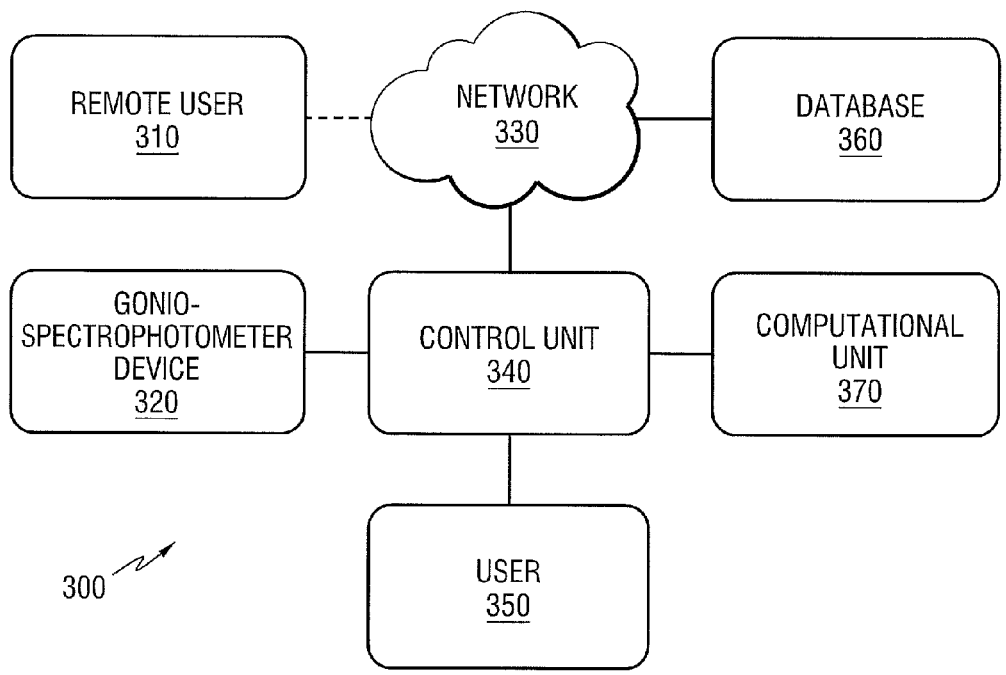
FIG. 3 illustrates an embodiment of a reflectance spectral analysis system that may be used for, for example, complex coating formula prediction.

FIG. 3 illustrates an embodiment of a reflectance spectral analysis system 300 that may be used for, for example, complex coating formula prediction. The system 300 may include a goniospectrophotometric device 320, such as an X-Rite MA98 Portable Multi-Angle Spectrophotometer sold by X-Rite Incorporated that may be in communication with a control unit 340. In various embodiments, the system 300 may include a database 360 that contains parameters for use by a computational unit 370, which may be in communication with the control unit 340 through a network 330. In various embodiments, the control unit 340 may be accessed by a remote user(s) 310 via the network 330. In various embodiments, the network 330 is the internet, an intranet, or any other type of suitable network. In various embodiments, the system 300 may be adapted to measure reflectances of a coated sample at several angles including, but limited to, three angles between the incident electromagnetic wave as illustrated in FIG. 1.

Figure 2:
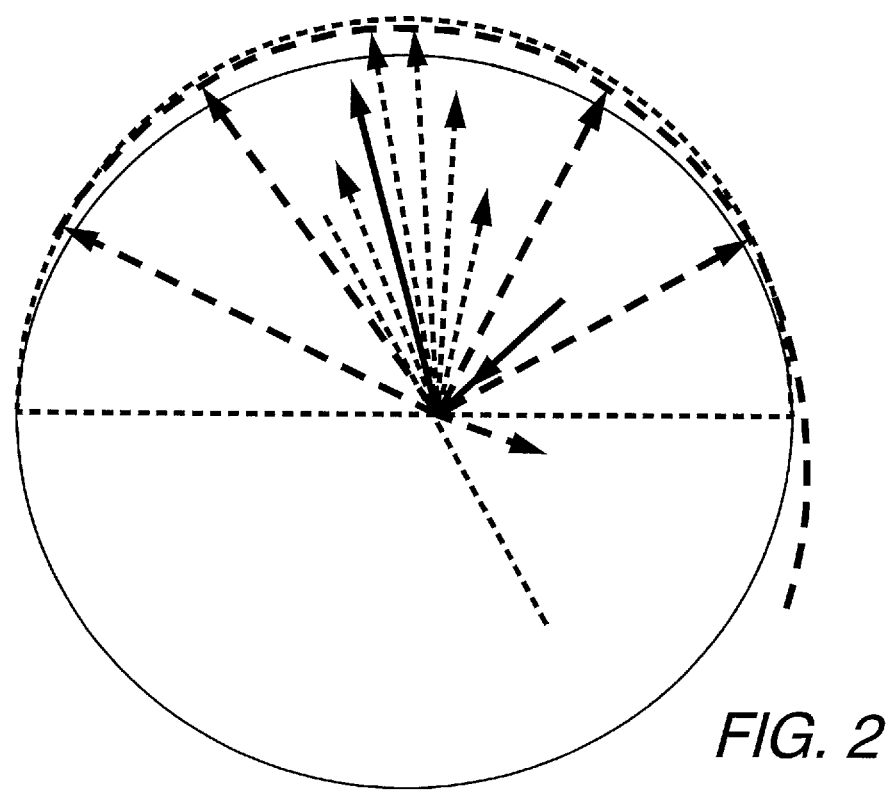
FIG. 2 illustrates reflectance data collected as an array of detectors spread throughout the angular geometry space.

Various embodiments of the invention may include reflectance data from "the out-of-plane" angles as illustrated in FIG. 2.

Based on reflectances, the absorption and scattering parameters of the electromagnetic wave may be determined at different parts of the spectrum. In one embodiment, the system 300 may be used in a color match setting to determine a metric of comparison. In various embodiments, the system 300 may be suited for such a setting as a formulation laboratory where color matching systems are sometimes inaccurate, difficult to control variation, or pose the potential for waste of materials through trial-and-error style color matching.

In various embodiments, the control unit 340 may includes rule sets to control operation of the goniospectrophotometric device 320. A user 350 may directly interface with the control unit 340 with, for example, an input device such as a touchscreen, a keyboard, a mouse, any type of pointing device, etc. The remote user or user(s) 310 may connect to the control unit 340 via the network 330. The control unit 340 may include a database or database server 360, such as a remote server with data storage. The control unit 340 may be configured to analyze data from the device 320. The control unit 340 may include a display device that displays the data in a raw form or an analyzed form. Also, the control unit 340 may form an automatically configured wireless network to which users 350 within a certain distance (e.g., inside a building/lab) may connect, e.g., via Bluetooth enabled devices such as notebook or tablet computers, personal data assistants, etc. In an embodiment, the control unit 340 includes a personal computer that includes a processor, memory and a communication port to enable communication with the goniospectrophotometric device 320.

The computational unit 370 may be configured to perform various radiative transfer calculations as described herein. The computational unit 370 may be, for example, any type of computer that includes an operating system and the appropriate software to perform the methods described herein. The computational unit 370 may include hardware such as an arithmetic logic unit, a parallel processor, etc. The computational unit 370 may include computer networking devices that allow the unit 370 to communicate via the network 330 to the control unit 340 and/or to the remote user(s) 310. In various embodiments, the computational unit 370 may be a sub-system of the control unit 340. In various embodiments, the computational unit 370 may use numerical methods to simulate and predict various reflectances under model conditions. Such model conditions may include masstone and various concentrations of calibration spray-out panels.

In various embodiments, the computational unit 370 receives boundary conditions related to an electromagnetic wave path in the goniospectrophotometric device 320. The boundary conditions may be received from, for example, a server or the users 310 or 350. The boundary conditions may relate to total internal reflection of the electromagnetic wave path within the target complex coating mixture. In various embodiments, the computational unit 370 may generate mesh data for a given wave model to be approached in the goniospectrophotometric device 320 and may compute electromagnetic propagation conditions based on prior data from the goniospectrophotometric device 320.

During operation, the goniospectrophotometric device 320 may take spectral reflectance data of a coated surface at multiple angles that may include, but not be limited to, the angles available between the incident electromagnetic wave and the specular reflection of that electromagnetic wave, based on control signals from the control unit 340. The reflectances may be sent to the control unit 340 via a direct link, for example a universal serial bus cable, or via the network 330. In various embodiments, the control unit 340 may analyze the spectral reflectance data to provide electromagnetic wave propagation data. The data may be presented as a visual representation or as raw data which may include numerical data. The users 310 and/or 350 may change certain optical parameters of the data from the goniospectrophotometric device 320 through the control unit 340.

Figure 4:
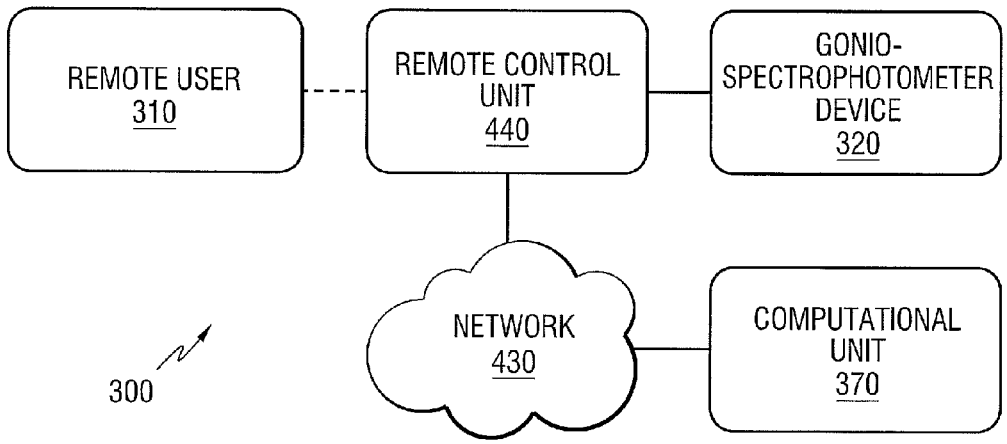
FIG. 4 illustrates another embodiment of a reflectance spectral analysis system that may be used for, for example, complex coating formula prediction.

In an embodiment of the system 300 illustrated in FIG. 4, the system 300 may include a network 430 in communication with the goniospectrophotometric device 320 through a remote control unit 440. The remote user(s) 310 may use the goniospectrophotometric device 320 local to the remote user(s) 310.

Figure 5:
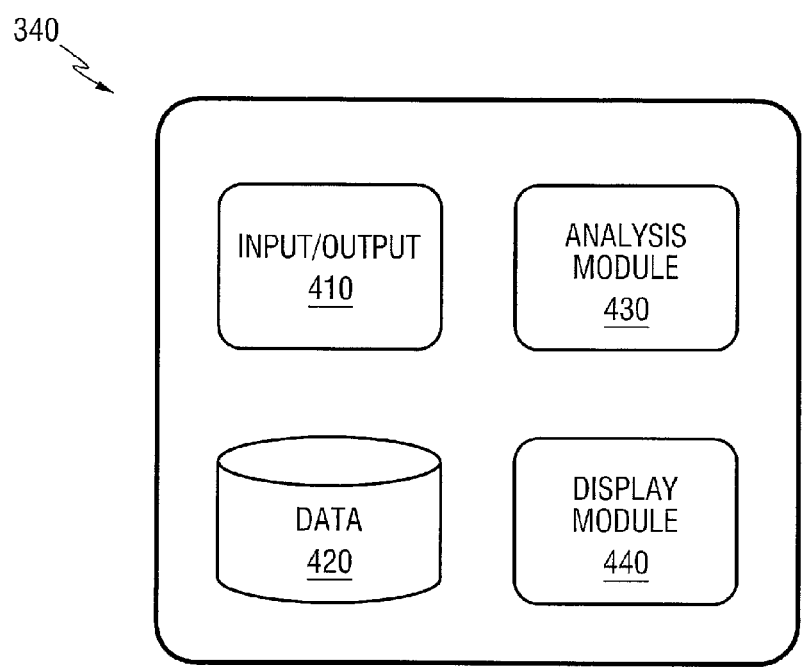
FIG. 5 illustrates an embodiment of the control unit of FIG. 3.

FIG. 5 illustrates an embodiment of the control unit 340 that is located remotely from the goniospectrophotometric device 320. The control unit 340 receives data from the goniospectrophotometric device 320 and instructions from the users 310 and/or 350. The data may be transmitted wirelessly or over a wired network. The control unit 340 may send control signals to the goniospectrophotometric device 320. In various embodiments, the control unit 340 may be a server with appropriate storage and rule sets.

The control unit 340 depicted in FIG. 4 may include an input/output module 410 that provides communication between modules in the unit 340 and other devices, such as communication over networks to the goniospectrophotometric device 320. The input/output module 410 may be adapted to receive multi-angle spectral reflectance data from the goniospectrophotometric device 320. The input/output module 410 may include data transfer devices such as a universal serial bus, a serial bus, a disk drive, or global computer connections such as to the Internet. In various embodiments, the input/output module 410 may include a network interface device to provide connectivity between the control unit 540 and a network using any suitable communications protocol. In various embodiments, the input/output module 410 may connect to one type of network or any number of networks of the same or different types.

The input/output module 410 may provide a digital key to the goniospectrophotometric device 320 to allow operation of the goniospectrophotometric device 320. The input/output module 410 in various embodiments may be adapted to provide communication with a variety of users such that, for example, a group of users may use the same goniospectrophotometric device 320 or a group of users may each individually use separate goniospectrophotometric devices 320 that communicate with the same control unit 340.

The control unit 340 may include a data storage 420 that stores raw data from the goniospectrophotometric device 320, optical parameters at the time of measuring the raw data, and analyzed data that has been processed according embodiments of the methods described herein. An analysis module 430 may apply analysis rule sets to the data stored in the data storage 420 to, for example, analyze electromagnetic wave propagation data in the data storage 420. In various embodiments, the analysis module 430 performs reflectance spectral analysis. The analysis module 430 may add color analysis to the spectral reflectances measured by the goniospectrophotometric device 320.

The control unit 340 may include a display module 440 that, in various embodiments, presents spectral reflectance data from the goniospectrophotometric device 320 and the preliminary analysis from the analysis module 430 in, for example, real-time or near real-time such that a data collection period may begin after the user observes that the system 300 is working and that good data can be acquired. The display module 440 may provide a user friendly and familiar interface between the hardware and software of the system 300, such that a user 350 can acquire meaningful data from the system 300.

The above described modules may reside in a single computer, or may be distributed across multiple computers connected via a network or a bus. A variety of user interfaces or front-end servers may receive requests and communicate with appropriate modules, and return replies. Front-end servers may connect to a variety of controllers which then may be connected to variety of devices. A variety of analysis servers or storage servers may also be used.

Figure 6:
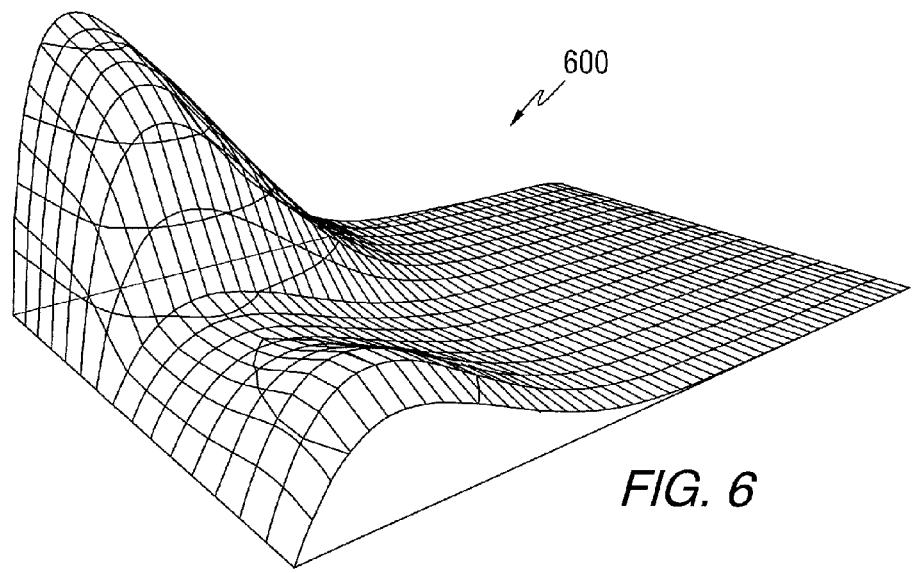
FIG. 6 is a visual representation of data acquired using the system of FIG. 3.

FIG. 6 is a visual representation of data 600 acquired using the system 300 described herein. The data 600 may be displayed on a display device such as a computer monitor or other display. The visual representation as shown in FIG. 6 is a vector field overlaid on a frame of data. The vector field is one presentation of data computed from the raw image data acquired by the goniospectrophotometric device 320. In various embodiments, other data may be computed from the experimental data acquired using the computational unit 370 and the control unit 340.

Figure 7A:
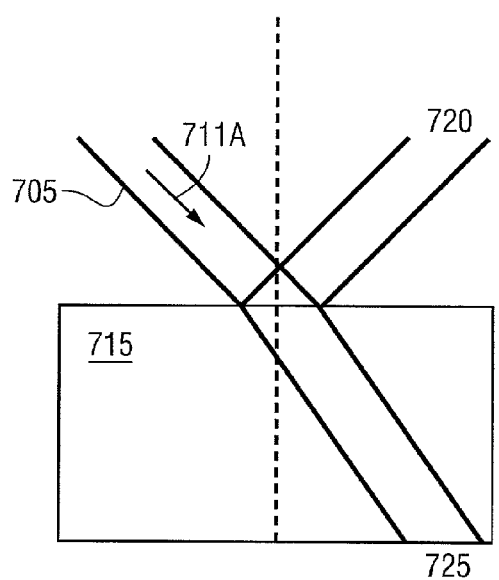
FIG. 7A illustrates the interaction between the electromagnetic wave and the complex paint mixture at 45 degree incidence.
Figure 7B:
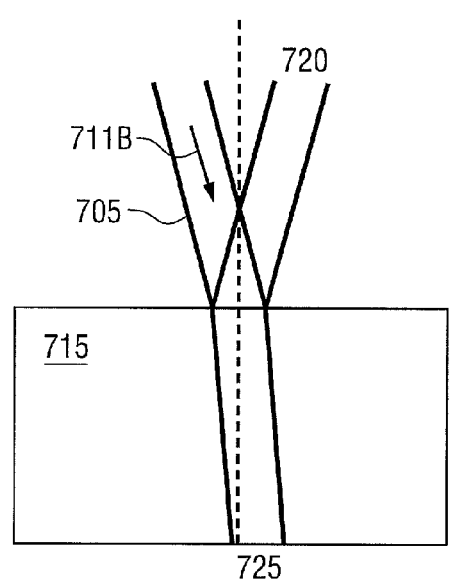
FIG. 7B illustrates the interaction between the electromagnetic wave and the complex paint mixture at 15 degree incidence.

FIGS. 7A and 7B illustrate a schematic view of an application of the system 300 of FIG. 3 that may be used to provide a visual tool for embodiments of the radiative transfer methods described herein. Each of FIGS. 7A and 7B schematically shows a portion of an electromagnetic path 705. The electromagnetic wave path portions 705 may be any portion of the electromagnetic path in the goniospectrophotometric device 320 described herein. In various embodiments, the electromagnetic wave path portions 705 shown in FIGS. 7A and 7B are positioned at the location where the goniospectrophotometric device 320 can acquire spectral reflectance data. FIG. 7A illustrates an application where the electromagnetic wave path is incident at 45 degrees from the normal. FIG. 7B illustrates an application where the electromagnetic wave path is incident at 15 degrees from the normal. Each of FIGS. 7A and 7B includes a complex coating mixture 715 within the electromagnetic wave path 705.

In embodiments, the electromagnetic wave path is reflected as illustrated in reflection 720. In various embodiments, the electromagnetic wave path is refracted as illustrated in refraction 725. The electromagnetic wave propagates in the direction of arrows 711A and 711B, respectively. The electromagnetic wave impinges on the surface of the complex coating 715, which faces the influx of the electromagnetic wave. As a result, the surface 715 deflects the electromagnetic wave upwardly away from the incident wave such that the electromagnetic wave can still travel rightward in the same manner, though at reduced intensity. The remaining intensity is deflected inwardly to the normal such the electromagnetic wave now travels rightward in an impeded manner.

Electromagnetic wave propagation can be described by fluxes and there are several types of fluxes. See, for example, "Classical Electrodynamics," J. D. Jackson, ISBN-10: 047130932X and "Radiative Transfer," S. Chandrasekhar, ISBN 0486605906, which are incorporated herein by reference.

Various embodiments consider a chromophore as a property of a complex coating mixture with a particular geometrical size, which constitutes absorption. This description is a schematized version of the real situation. However, the resolution of the goniospectrophotometric device 320 allows the model to work sufficiently, and it provides the essence of the absorption coefficient, the parameter that may be used to describe the effectiveness of absorption. The absorption coefficient describes any medium containing many chromophores at a concentration described as a volume density. In various aspects, the size of the absorption may be smaller or larger than the geometrical size of the chromophore. In various embodiments, an auxochrome model is applied to the absorption parameter.

Embodiments of the present invention are useful regardless of whether the electromagnetic wave path is a straight line or a highly tortuous path due to multiple scattering in an optically turbid medium.

Various aspects of the invention consider a scattering particle as a property of the target complex coating mixture with a particular geometrical size, for example that this property redirects incident electromagnetic waves into new directions and so prevents the forward on-axis transmission of the electromagnetic wave. The resolution of the goniospectrophotometric device 320 provides the essence of the scattering coefficient, a parameter analogous to the absorption coefficient discussed herein.

In various embodiments, the size of the scattering may be smaller or larger than the geometrical size of the scattering particle. The scattering coefficient describes any medium containing many scattering particles at a concentration described as a volume density.

The anisotropy is a measure of the amount of forward direction retained after a single scattering event. An electromagnetic wave is scattered by a particle so that its trajectory is deflected by a deflection angle. The component of the new trajectory is aligned in the forward direction. A scattering event causes a deflection at angle from the original forward trajectory. An azimuthal angle of scattering is also present.

Various aspects of the invention take an approach to radiative transfer theory as an extension of the method used for complex coating mixtures without effect pigments involving Kubelka-Munk theory. The directional nature of the electromagnetic wave scattering in complex coating mixtures containing effect pigments, such as aluminium and pearlescent pigments, may be taken into account and used in conjunction with the goniospectrophotometric device 320 to derive a formula for an unknown complex coating mixture.

Electromagnetic scattering in metallic and pearlescent coatings is often a complex problem because of the different scattering characteristics of the effect flakes, for example aluminium flakes, and the conventional solid pigments used in complex paint mixtures. Solid pigments diffuse the electromagnetic wave and produce an approximately Lambertian appearance, that is, reflectance independent of viewing angle. For this reason, a simplified Kubelka-Munk approximation may be appropriate for solid toners but is often inadequate for formulating complex coating mixtures that contain metallic, pearlescent, and other special effect pigments.

Conversely, metallic and pearlescent pigments produce a strongly angle-dependent appearance, for example the mirror like reflection from aluminium flakes. The flakes are not all aligned parallel to the coated substrate, but there is a distribution of alignments which determines the shape and height of the peak in the reflectance around the specular angle. Because of the variable angular reflection of the complex coating mixture containing effect pigments, even a masstone aluminium, for example, will have non-negligible multiple scattering, and thus simplified approaches often fail, for example as seen with Mie theories.

In a complex coating mixture the multiple scattering from conventional pigments broadens and lowers the specular peak formed by the effect pigments. Absorption by conventional pigments tends to lower the reflectance profile produced by the effect pigments.

Light is an electromagnetic phenomenon and obeys a vectorial wave equation for a field. The scattering behavior may then be determined once the spatial distribution of the dielectric constant of the material is known. However, if the dielectric material is a complex coating mixture containing effect pigments in which there are a large number of scattering centers, the phase information contained in the fields may be treated separately from the intensities. Similarly, a multiplicity of scatterings allows for the polarization dependence of the electromagnetic wave to be treated in the same manner as the phase components. In various embodiments, the treatment of the polarization components is handled using complex calculations for complex coating mixtures containing special effect pigments which in single scattering have polarization-dependent profiles, for example microfine $TiO_2$ and pearlescent pigments.

The radiative transfer equation may be derived from fundamental electromagnetic scattering equations. In various embodiments, a phenomenological point of view may be used and an equation is set up to describe the balance of radiant fluxes in a small volume of the scattering medium.

In embodiments, the granularity of the medium and the relationships between the positions of scattering particles are separated and treated in a similar manner as the phase information of the scattering events.

Various aspects of the invention consider the situation of radiation of intensity incident on a pillbox of miniscule thickness 715, as illustrated in FIGS. 7A and 7B.

As used herein, intensity may be defined as the electromagnetic power per unit area per unit solid angle such that fluxes which arise from multiply scattered electromagnetic radiation may be handled. The intensity is reduced in the pillbox by the processes of absorption and scattering out of the pillbox, but also is added to by scattering into the pillbox from directions perpendicular to the electromagnetic wave.

The radiative transfer equation used in various embodiments describes such a balance:

$$\frac{1}{c}\frac{\partial}{\partial t}I_v + \hat{\Omega}\cdot\nabla I_v + (\sigma_v + \alpha_v)I_v = \frac{1}{4\pi c}\sigma_v \int I_v d\Omega \qquad (2)$$

The attenuation terms $\sigma_v$ and $\alpha_v$ are the scattering cross section and the absorption, respectively. Both the absorption and scatting are dependent on the direction of travel relative to the substrate normal. This manifests itself as a difference between a complex coating mixture containing effect pigments and a complex coating mixture without such pigments. Electromagnetic rays travelling perpendicularly to the substrate are strongly attenuated because of the large cross section presented to them by the effect flakes. On the other hand, rays travelling parallel to the substrate slip through the flakes and attenuation is low. Various embodiments may use such a difference and require reflectance data from the goniospecrophotometric device 320 with an illumination source such that incident radiation travels near-parallel to the substrate.

In various embodiments, the attenuation coefficients are broken into zenithal and azimuthal components and are treated separately in order to look at the effect of gravity on flake alignment, such as the settling of flakes in the spraying and drying process.

Figure 8:
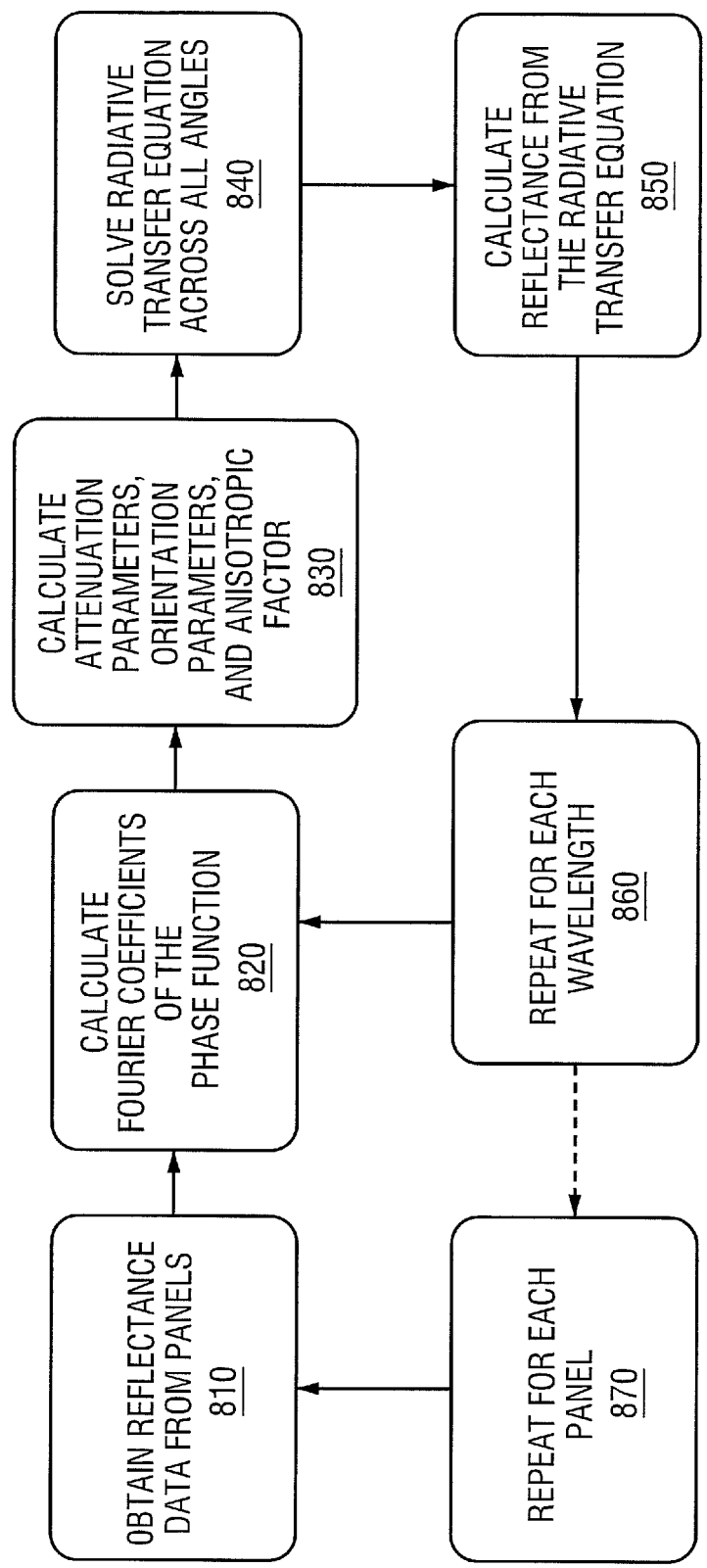
FIG. 8 illustrates an embodiment of a process that calculates radiative transfer parameters for calibration panels.

FIG. 8 illustrates an embodiment of a process that calculates radiative transfer parameters from calibration panels. At step 810 reflectance data is obtained from the panels and at step 820, Fourier coefficients of the phase function are calculated using an orientation distribution function. Various embodiments use a scattering function, which is a probability distribution of the incident scattering angle. Such a distribution is a complex function given by Mie theory or by any suitable generalization. The fine details of the phase function at step 820 may be mostly washed out by the effects of multiple scattering.

At step 830 attenuation and orientation parameters and an anisotropic factor are calculated. For complex coating mixtures without effect pigments, the attenuation parameter is equal to unity because the attenuation, scattering and absorption, is independent of the incident scattering angle. Geometrical optics may be used to describe the properties of effect pigments. The orientation of an effect flake may be calculated using an orientation distribution function at step 830.

At step 840 the full radiative transfer equation (Equation 1 hereinabove) is solved. The function interpolates smoothly between various extremes of scattering behavior and encompasses the scattering diagram of solid pigments.

In various embodiments, when an interference particle is present, the use of Fresnel equations gives the optical properties accurately. In the formula for attenuation the generalization for pearlescent pigments may include transmittance parameters of the pigment particle calculated in a similar way to reflectivity.

At step 850, in various embodiments auxiliary integral equations are derived for which the equations for the reflectance are readably solvable. Standard numerical techniques may be applied to these equations, for example use of the Gaussian quadrature in situations for a given order where the integrand is a polynomial. In various embodiments, a non-linear least squares fit of the reflectance data from known panels to the equations of the mathematical model may be used.

At step 860, steps 820, 830, 840 and 850 are repeated for each measured wavelength and at step 870 the entire process is repeated for each panel.

Figure 9:
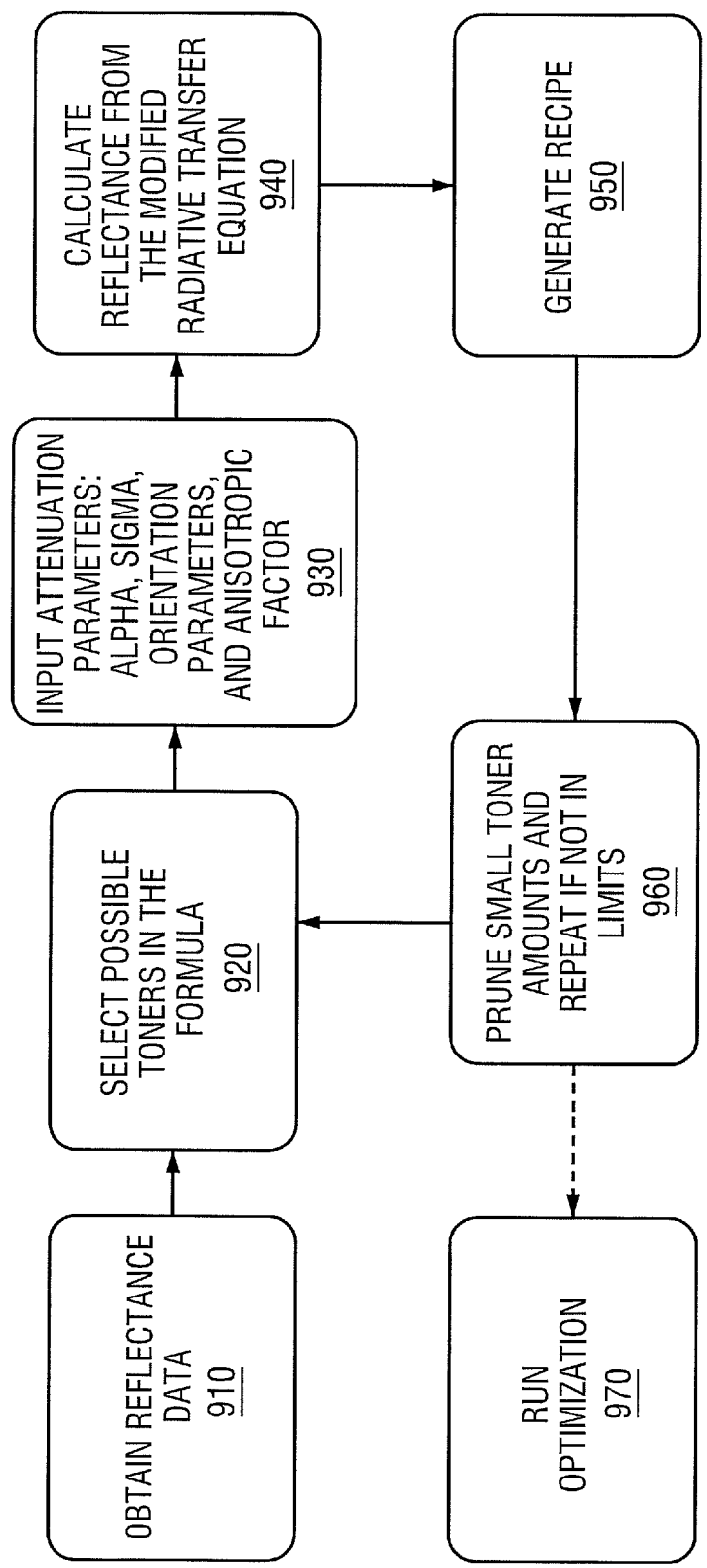
FIG. 9 illustrates an embodiment of a process that calculates a formula for a target complex coating.

FIG. 9 illustrates an embodiment of a process of determining a formula of a target complex coating. At step 910, reflectance data is obtained from the target coating and at step 920 a list of possible toners is selected. At step 930, the attenuation parameters that were calculated at step 830 in FIG. 8 are input and at step 940 a modified radiative transfer equation is used to calculate reflectance. Such an equation may use attenuation approximations that apply specifically, for example, to automotive coatings.

At step 950, the recipe (i.e., the formulation or approximate formulation of the target coating) is generated. At step 960 a combinatorial method may be used to prune out small toner amounts. At step 970, optimization is performed to ensure that the formulation is at least acceptable.

Figure 10:
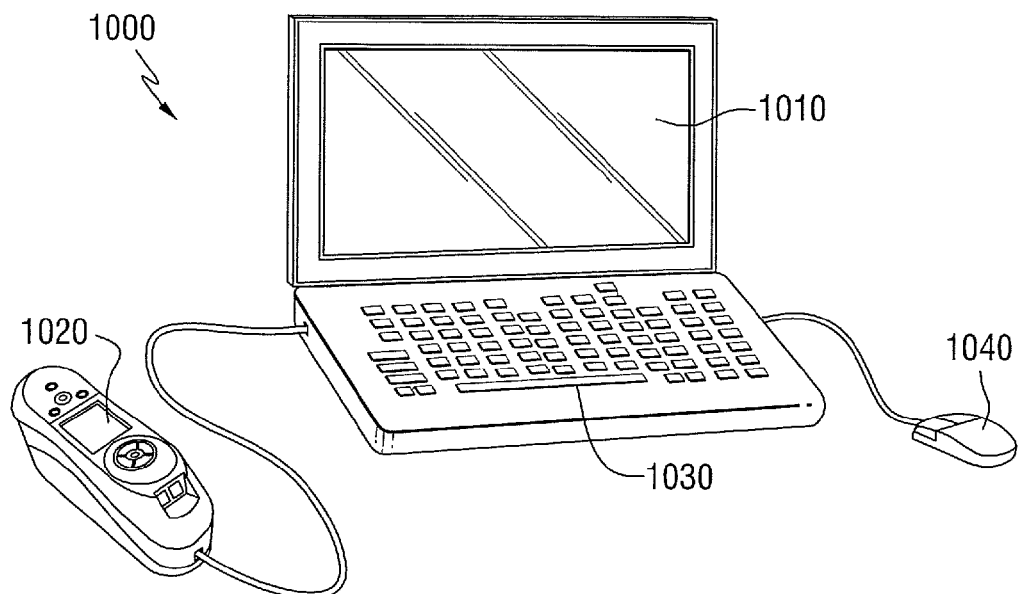
FIG. 10 illustrates an embodiment of a system in which the processes of embodiments of the present invention may be used.

An embodiment of a system 1000 in which the processes of embodiments of the present invention may be used is illustrated in FIG. 10. A processing unit 1010, such as a laptop, notebook, or tablet computer, receives input data from a goniospectrophotometric device 1020, such as, for example, an X-Rite MA98 Portable Multi-Angle Spectrophotometer sold by X-Rite Incorporated. The system 1000 may include an electronic switch input device 1030, such as a computer keyboard, and a pointing device 1040, such as a computer mouse.

Figure 11:
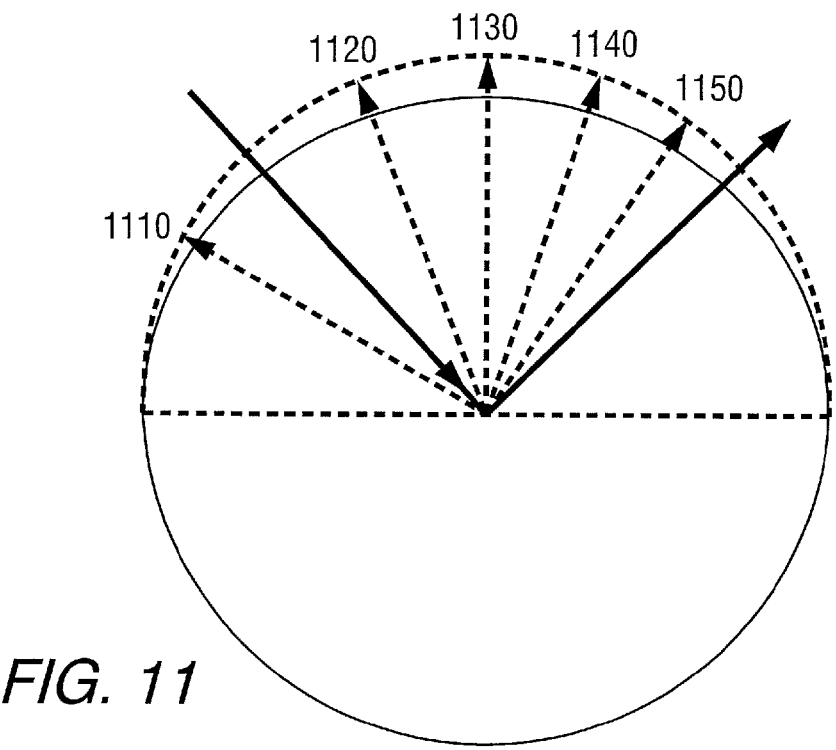
FIG. 11 illustrates a series of goniospectrophotometric devices with five limited angles.

In various embodiments, the primary data from the goniospectrophotometric device 1020 may be limited to industry standard "in-plane" angle detectors, as illustrated in FIG. 11. FIG. 11 illustrates a series of goniospectrophotometric devices with five limited angles. The angles are measured from the surface of a complex coating mixture at 155 degrees (1110), 120 degrees (1120), 90 degrees (1130), 70 degrees (1140), and 60 degrees (1150).

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Accordingly, the particular embodiments described in detail herein are illustrative only and are not limiting to the scope of the invention.

What is claimed is:

1. A computer implemented method, comprising:
receiving through a digital communication channel, from a spectrophotometer, reflectance data from a calibration panel;
calculating, with a processing device, Fourier coefficients of a phase function associated with the reflectance data from the calibration panel, wherein the phase function is associated with a portion of a radiative transfer equation;
calculating, with the processing device, attenuation and orientation parameters and an anisotropic factor for the calibration panel, wherein the attenuation parameters comprise a scattering cross section and absorption determined from the reflectance data received from the spectrophotometer;
determining a solution to the radiative transfer equation for the calibration panel, wherein the radiative transfer equation comprises portions associated with the Fourier coefficients of the phase function, the attenuation and orientation parameters, and the anisotropic factor;
receiving through a digital communication channel, from a spectrophotometer, reflectance data from a target coating;
selecting a list of possible toners that are present within the target coating;
calculating a reflectance of the possible toners, based upon the attenuation parameters and a modified radiative transfer equation; and
generating, using the processing device and based on the calculated reflectance of the possible toners, a coating formulation that is the same or substantially similar in appearance to the target coating, wherein the coating formulation utilizes one or more of the possible toners.

2. The method of claim 1, further comprising optimizing the coating formulation.

3. The method of claim 1, further comprising calculating a plurality of radiative transfer parameters from reflectance data obtained from the calibration panel.

4. The method of claim 1, further comprising changing the coating formulation by removing at least one toner from the coating formulation.

5. A system, comprising:
a database; and
a processor in communication with the database and programmed to:
receive through a digital communication channel, from a spectrophotometer, reflectance data from a target coating;
select a list of possible toners that are present within the target coating;
calculate a reflectance of the possible toners, based upon attenuation parameters and a modified radiative transfer equation, wherein the attenuation parameters are calculated from a calibration panel; and
generate, using the processor and based on the calculated reflectance of the possible toners, a coating formulation that is the same or substantially similar in appearance to the target coating, wherein the coating formulation utilizes one or more of the possible toners.

6. The system of claim 5, wherein the processor comprises an analysis module, a display module, and an input/output module.

7. The system of claim 5, wherein the processor is further programmed to optimize the coating formulation.

8. The system of claim 5, wherein the processor is further programmed to calculate a plurality of radiative transfer parameters from reflectance data obtained from the calibration panel.

9. The system of claim 5, wherein the processor is further programmed to:
- calculate, with the processor, Fourier coefficients of a phase function associated with the reflectance data from the calibration panel, wherein the phase function is associated with a portion of a radiative transfer equation;
- calculate, with the processor, attenuation and orientation parameters and an anisotropic factor for the calibration panel, wherein the attenuation parameters comprise a scattering cross section and absorption determined from the reflectance data received from the spectrophotometer; and
- determine a solution to the radiative transfer equation for the calibration panel, wherein the radiative transfer equation comprises portions associated with the Fourier coefficients of the phase function, the attenuation and orientation parameters, and the anisotropic factor.

10. An apparatus, comprising:
- means for receiving through a digital communication channel, from a spectrophotometer, reflectance data from a calibration panel;
- means for calculating, with a processing device, Fourier coefficients of a phase function associated with the reflectance data from the calibration panel, wherein the phase function is associated with a portion of a radiative transfer equation;
- means for calculating, with the processing device, attenuation and orientation parameters and an anisotropic factor for the calibration panel, wherein the attenuation parameters comprise a scattering cross section and absorption determined from the reflectance data received from the spectrophotometer;
- means for determining a solution to the radiative transfer equation for the calibration panel, wherein the radiative transfer equation comprises portions associated with the Fourier coefficients of the phase function, the attenuation and orientation parameters, and the anisotropic factor;
- means for receiving through a digital communication channel, from a spectrophotometer, reflectance data from a target coating;
- means for selecting a list of possible toners that are present within the target coating;
- means for calculating a reflectance of the possible toners, based upon the attenuation parameters and a modified radiative transfer equation; and
- means for generating, based on the calculated reflectance of the possible toners, a coating formulation that is the same or substantially similar in appearance to the target coating, wherein the coating formulation utilizes one or more of the possible toners.

11. The apparatus of claim 10, further comprising means for optimizing the coating formulation.

12. The apparatus of claim 10, further comprising means for calculating a plurality of radiative transfer parameters from reflectance data obtained from the calibration panel.

13. A non-transitory computer readable medium including software, which when executed by a processor, causes the processor to:
- receive through a digital communication channel, from a spectrophotometer, obtain reflectance data from a calibration panel;
- calculate, with a processing device, Fourier coefficients of a phase function associated with the reflectance data from the calibration panel, wherein the phase function is associated with a portion of a radiative transfer equation;
- calculate, with the processing device, attenuation and orientation parameters and an anisotropic factor for the calibration panel, wherein the attenuation parameters comprise a scattering cross section and absorption determined from the reflectance data received from the spectrophotometer;
- determine a solution to the radiative transfer equation for the calibration panel, wherein the radiative transfer equation comprises portions associated with the Fourier coefficients of the phase function, the attenuation and orientation parameters, and the anisotropic factor;
- receive through a digital communication channel, from a spectrophotometer, reflectance data from a target coating;
- select a list of possible toners that are present within the target coating;
- calculate a reflectance of the possible toners, based upon the attenuation parameters and a modified radiative transfer equation; and
- generate, based on the calculated reflectance of the possible toners, a coating formulation that is the same or substantially similar in appearance to the target coating, wherein the coating formulation utilizes one or more of the possible toners.

14. The medium of claim 13, further comprising software for causing the processor to optimize the coating formulation.

15. The medium of claim 13, further comprising software for calculating a plurality of radiative transfer parameters from reflectance data obtained from the a processor in communication with the database and programmed to calibration panel.

* * * * *